United States Patent [19]

Parhi

[11] Patent Number: 4,584,383
[45] Date of Patent: Apr. 22, 1986

[54] SUBSTITUTED 2-MERCAPTO-IMIDAZOLES AND THEIR PREPARATION

[75] Inventor: Seppo S. L. Parhi, Kiviniemi, Finland

[73] Assignee: Farmos Yhtyma-Oy, Turku, Finland

[21] Appl. No.: 661,487

[22] Filed: Oct. 16, 1984

[30] Foreign Application Priority Data

Oct. 18, 1983 [FI] Finland .............................. 833794

[51] Int. Cl.$^4$ .................... C07D 401/06; C07D 233/84
[52] U.S. Cl. .................................. 546/278; 548/321; 549/379
[58] Field of Search ...................... 548/321; 546/278

[56] References Cited

U.S. PATENT DOCUMENTS 2,541,924  2/1951  Jones ................................. 548/321

FOREIGN PATENT DOCUMENTS 0024829  3/1981  European Pat. Off. ............ 548/343
0058047  8/1982  European Pat. Off. ............ 548/342
196869   7/1967  U.S.S.R. .............................. 548/321

OTHER PUBLICATIONS

Jackman, M., et al., *J. Am. Chem. Soc.*, 70, 2884 (1948).
L. Sattler, *Adv. Carbohydr. Chemistry* 3 (1948), 113.
K. Heyns et al., *Z. Naturforsch.* 76 (1952), 486.
F. Garcia Gonzales, et al., *Anales Real. Soc. Espan. Fis. y. Quim*, 44 B (1948), 233.
G. Huber et al., *Helv. Chim Acta* 43 (1960), 713 and 1787.
R. A. F. Bullerwell et al., *J. Chem. Soc.* 1951, 3030.

*Primary Examiner*—Richard A. Schwartz
*Attorney, Agent, or Firm*—Armstrong, Nikaido, Marmelstein & Kubovcik

[57] ABSTRACT

The invention provides novel 1-substituted-5-hydroxymethyl-2-mercapto-imidazoles of the formula

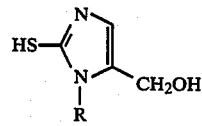

(I)

wherein R is pyridylmethyl, alkyl of 1 to 4 carbon atoms, or a radical of formula:

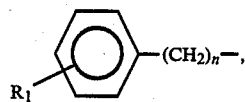

in which $R_1$ is hydrogen or halogen and n is 1–3. These compounds are prepared by reacting together dihydroxyacetone dimer, the amine R—NH$_2$, and potassium thiocyanate. The compounds of formula (I) are useful as starting materials in the preparation of known therapeutically valuable imidazole derivatives, by removing the mercapto group, oxidizing the alcohol group to an aldehyde group and condensing the aldehyde with an appropriate phenyl or phenylalkyl magnesium halide.

4 Claims, No Drawings

SUBSTITUTED 2-MERCAPTO-IMIDAZOLES AND THEIR PREPARATION

This invention relates to substituted imidazole derivatives useful in the preparation of phenylethylimidazole derivatives of therapeutic interest and to their preparation and use.

A number of substituted phenylethylimidazole derivatives of therapeutic interest are known. For example in our European Specification No. 24829 we have described compounds of the formula:

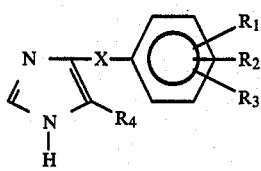

wherein $R_1$, $R_2$ and $R_3$, which can be the same or different, are each selected from hydrogen, chloro, bromo, fluoro, methyl, ethyl, methoxy, amino, hydroxy and nitro but are not all hydrogen; $R_4$ is hydrogen or alkyl of 1 to 7 carbon atoms:

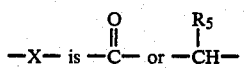

wherein $R_5$ is hydrogen, hydroxy or —$OR_6$ and $R_6$ is alkyl of 1 to 7 carbon atoms or phenyl; and their non-toxic pharmaceutically acceptable acid addition salts and mixtures thereof. These compounds are useful particularly as antihypertensive and anti-ulcer agents, and also as diuretic, sedative, analgesic, anti-inflammatory and tranquillizing agents.

In our European Specification No. 58047, we have described compounds of the formula:

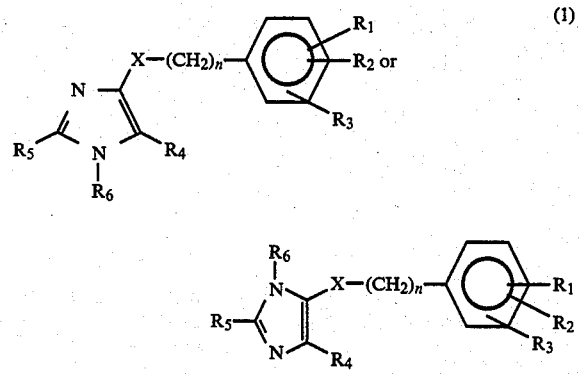

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or a substituted or unsubstituted benzyl; X is —$CH_2$—; —CHOH— or —CH=CH—; and n is 0–4, provided that $R_5$ and $R_6$ are simultaneously hydrogen only when n is 4 and X is —CH=CH— and when n is 0, X is —$CH_2$—, $R_1$, $R_2$, $R_3$ and $R_6$ are all hydrogen, and $R_4$ is hydrogen or ethyl, then $R_5$ is other than methyl or phenyl; when n is 0, X is CHOH, and $R_1$, $R_2$, $R_3$ and $R_4$ are all hydrogen, both of $R_5$ and $R_6$ are other than methyl; and when n is 2, X is CHOH, $R_1$, $R_2$, $R_4$ and $R_5$ are all hydrogen, and $R_6$ is methyl, then $R_3$ is other than 2-amino, and their non-toxic, pharmaceutically acceptable acid addition salts. These compounds have anti-thrombotic, anti-hypertensive, and β-blocking activity and also have anti-microbial and anti-fungal properties.

The present invention provides novel 1-substituted-5-hydroxymethyl-2-mercapto-imidazoles of the formula

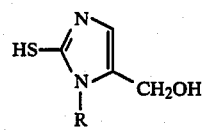

in which R is pyridylmethyl, alkyl of 1 to 4 carbon atoms, or a radical of formula:

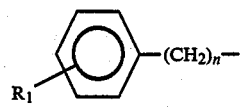

in which $R_1$ is hydrogen or halogen and n is 1–3, which are valuable intermediates in the preparation of phenylethyl imidazoles of the aforesaid types, including in particular 4(5)-(2,3-dimethylbenzyl)-imidazole which, in the form of the base, has the formula:

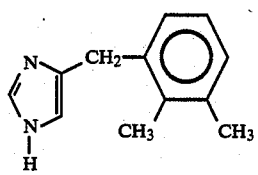

The compounds of the formula (I) are novel. A compound of formula (I) wherein R=H is known from R. A. F. Bullerwell et al., J.Chem.Soc. 1951, 3030. This known compound was obtained by the reaction of serine with potassium thiocyanate and sodium amalgam.

The compounds of the invention can occur as free bases or acid addition salts such as, for example, hydrochlorides, acetates, and sulfates.

According to the present invention the new 2-mercapto-imidazole derivatives of formula (I) are prepared by a new adaptation of two previously known reactions. They are the Art Lobry de Bruyn-Alberda von Ekenstein rearrangement for the preparation of D-glucosamine derivatives (L Sattler, Adv. Carbohydr. Chemistry 3 (1948) 113 and K Heyns et al., Z. Naturforsch. 76 (1952) 486), and the process for the preparation of alfa-mercaptoglucimidazoles from glucosamine and potassium thiocyanate (F García Gonzáles and J Fernández Bolanos, Anales Real. Soc. Espan. Fis. y Quim. 44 B (1948) 233; G Huber et al., Helv. Chim. Acta 43 (1960) 713 and 1787).

The process of the present invention comprises reacting dihydroxyacetone dimer (III), with an amine of formula $RNH_2$ to give the aminoaldehyde (II), which cyclizes with potassium thiocyanate in the presence of an acid to give the imidazole derivative of formula I. The process may be represented as follows:

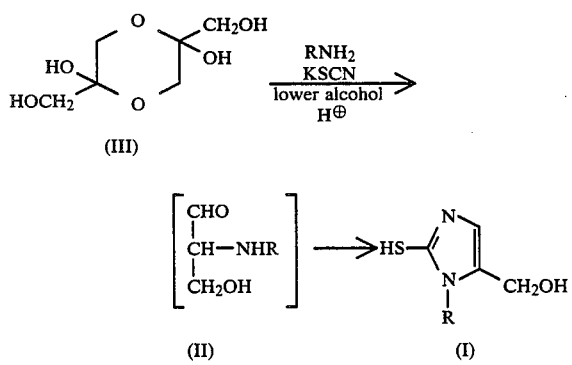

This synthesis conveniently takes place in one stage. Dihydroxyacetone dimer, the amine and potassium thiocyanate are combined in a lower alcohol, e.g. an alkanol of 1 to 4 carbon atoms, and are reacted in the presence of an acid. The reaction temperature can range from 10° to 100° C. The yield is excellent.

When the compounds of the invention are used to prepare compounds of medicinal interest such as those mentioned above, the mercapto group is first removed by oxidation preferably with nitric acid and the alcohol obtained is oxidized, e.g. with manganese dioxide, to the corresponding aldehyde. The N-substituted imidazole carboxaldehyde obtained may then be reacted with a Grignard reagent to prepare a 1,5-imidazole derivative and the protecting group of the N-atom can be removed to give a 4(5)-mono-substituted imidazole.

The invention thus includes within its scope a process for preparing the valuable aldehyde intermediate of formula:

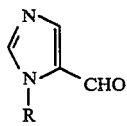

wherein R is as hereinbefore defined, which comprises reacting a compound of formula I with an oxidizing agent to remove the mercapto group and oxidizing the alcohol group in the product to an aldehyde group.

More particularly, to prepare the pharmacologically active imidazole compounds described in the European Specification No. 0024829 or 0058047, the mercapto group can be removed in a first step from a compound of formula (I) by treatment with dilute nitric acid with stirring at about 30°–35° C. The alcohol is then oxidized to the aldehyde with an appropriate oxidizing agent such as manganese dioxide for example by boiling in dioxane for 6 hours. In the third step a substituted phenyl- or phenylethyl-magnesium halide, usually bromide, is reacted with the above mentioned aldehyde in tetrahydrofuran to give the pharmacologically interesting 1,5-imidazole derivative. When the 1-substituent is a hydrogenolysable substituted or unsubstituted benzyl group, the 4(5)-substituted imidazole can be obtained by hydrogenation. The hydrogenation can be performed, e.g., in dilute acid solution at an elevated temperature.

The following Examples illustrate the invention. Example 1 describes the new intermediates and Example 2 their use.

EXAMPLE 1

1-Benzyl-2-mercapto-5-hydroxymethyl-imidazole n-Butanol (50 ml), glacial acetic acid (25 g), dihydroxyacetone dimer (21.0 g), potassium thiocyanate (34.1 g) and benzylamine (28.0 g) are combined at room temperature. The mixture is stirred at room temperature for 50 hours and the product is filtered. A light brown product is obtained, 35.0 g (68.2%), m.p. 229°–231° C. The NMR spectrum shows:

13c NMR (DMSO-d6, TMS): 46.35, 53.22, 112.46. 112.61, 126,69 127.02, 128.20, 130.20, 136.92, 162.53.

By using the same process with an appropriate amine starting material the following products can be prepared:

1-(4-chlorobenzyl)-2-mercapto-5-hydroxymethyl-imidazole, m.p. 217°–222° C.
1-(2-phenylethyl)-2-mercapto-5-hydroxymethyl-imidazole, m.p. 202°–208° C.
1-(2-pyridylmethyl)-2-mercapto-5-hydroxymethyl-imidazole, m.p. 181°–185° C.
1-ethyl-2-mercapto-5-hydroxymethyl-imidazole, m.p. dec. (175°–250° C.).

EXAMPLE 2

4-(2,3-dimethylbenzyl)-imidazole hydrochloride

1-Benzyl-2-mercapto-5-hydroxymethyl-imidazole (7.5 g) is added in small portions to a mixture of water (18 ml) and concentrated nitric acid (7.5 g) at 35° C. The mixture is stirred for 3 hours and the pH of the reaction mixture adjusted to 9–10 with sodium hydroxide. 1-Benzyl-5-hydroxymethyl-imidazole is obtained, 3.8 g (60%), m.p. 131°–135° C.

1-Benzyl-5-hydroxymethyl-imidazole (4.5 g), activated Mn O2 (8.5 g) and dioxane (25 ml) are mixed. The mixture is stirred at 90° C. for 6 hours, filtered and evaporated to dryness. The product, 1-benzyl-5-carboxaldehyde, crystallized from acetone as white crystals. Yield 3.58 g (80%), m.p. 52°–54° C.

2,3-Dimethylphenylmagnesium bromide (40 g), prepared in known manner, in 500 ml tetrahydrofuran is added dropwise to a tetrahydrofuran solution of 1-benzyl-5-carboxaldehyde (12 g). The reaction mixture is stirred for 5 hours and poured into ice-water (170 ml). Then is stirred and filtered. White 1-benzyl-5-[α-(2,3-dimethylphenyl)-hydroxymethyl]-imidazole HCl-salt is obtained in this way, 18.2 g (85%). The product can be recrystallized from, e.g., isopropanol.

1-Benzyl-5-[α-(2,3-dimethylphenyl)hydroxymethyl]-imidazole hydrochloride (17 g), 1N HCl solution (190 ml) and Pd/C catalyst are mixed. The mixture is hydrogenated in the usual way at normal pressure at 60° C. until no more hydrogen is consumed. The catalyst is filtered off and the filtrate made alkaline with sodium hydroxide. The product is filtered and dried. The product can be converted into the hydrochloride salt with HCl-isopropanol in ethyl acetate, m.p. 154°–159° C. Yield 8 g (70%).

I claim:

1. A 1-substituted-5-hydroxymethyl-2-mercaptoimidazole of the formula

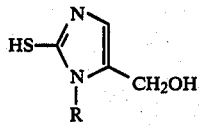

or an acid addition salt thereof, wherein R is pyridylmethyl, alkyl of 2 to 4 carbon atoms, or a radical of formula:

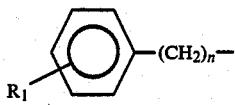

in which $R_1$ is hydrogen or halogen and n is 1–3.

2. A substituted imidazole according to claim 1 in which R is benzyl, 4-chlorobenzyl, 2-phenylethyl, 2-pyridylmethyl, or ethyl.

3. A substituted imidazole according to claim 1 which is 1-benzyl-2-mercapto-5-hydroxymethyl-imidazole.

4. A process for the preparation of a compound as claimed in claim 1 which comprises reacting dihydroxyacetone dimer with potassium thiocyanate and a primary amine of formula:

$$RNH_2 \qquad (V)$$

wherein R is as defined in claim 1, in a lower alcohol in the presence of an acid at a temperature of 10°–100° C.

* * * * *